United States Patent [19]

Mahoney et al.

[11] 4,434,000
[45] Feb. 28, 1984

[54] N-(BENZENESULFONYL) CARBAMATES HERBICIDAL ANTIDOTES

[75] Inventors: Martin D. Mahoney, Lansing, Mich.; Edmund J. Gaughan, Berkeley, Calif.; Ferenc M. Pallos; Hsiao-Ling Lam, both of Walnut Creek, Calif.

[73] Assignee: Stauffer Chemical Company, Westport, Conn.

[21] Appl. No.: 69,486

[22] Filed: Aug. 24, 1979

[51] Int. Cl.³ .................... A01N 43/00; A01N 37/18; A01N 47/30
[52] U.S. Cl. .......................... 71/103; 71/88; 71/91; 71/98; 71/118; 71/120
[58] Field of Search .......................... 71/118, 103, 120

[56] References Cited

U.S. PATENT DOCUMENTS

| | | | |
|---|---|---|---|
| 3,816,498 | 6/1974 | Teach | 71/118 |
| 4,021,229 | 5/1977 | Arneklev et al. | 71/103 |
| 4,168,152 | 9/1979 | Gaughan et al. | 71/103 |
| 4,230,874 | 10/1980 | Pallos et al. | 71/70 |

FOREIGN PATENT DOCUMENTS 846894 4/1977 Belgium ......................... 71/103

Primary Examiner—Glennon H. Hollrah

Attorney, Agent, or Firm—Harry A. Pacini

[57] ABSTRACT

Compositions comprise an urea herbicide and a N-(benzenesulfonyl) carbamate of the formula

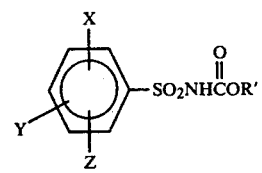

in which
X and Y are independently selected from the group consisting of hydrogen and methyl;
Z is selected from the group consisting of hydrogen, methyl, chloro, and trifluoromethyl; and
R' is selected from the group consisting of 1-4 carbon alkyl, 1-4 carbon haloalkyl, 3-6 carbon alkenyl, 3-6 carbon haloalkenyl, 3-6 carbon alkynyl, cyanoethylthioethyl, 2-6 carbon alkoxyalkyl, diethylhydroxylamine, acetoxime, methylthioacetimidate, substituted phenyl, substituted benzyl, and sulfolane.

10 Claims, No Drawings

N-(BENZENESULFONYL) CARBAMATES HERBICIDAL ANTIDOTES

BACKGROUND OF THE INVENTION

Uses of Herbicides

An herbicide is a compound which controls or modifies plant growth, e.g., killing, retarding, defoliating, desiccating, regulating, stunting, tillering, stimulating, and dwarfing. "Plant" refers to all physical parts, including seeds, seedlings, saplings, roots, tubers, stems, stalks, foliage, and fruits. "Plant growth" is meant to include all phases of development from seed germination to natural or induced cessation of life.

Herbicides are generally used to control or eradicate undesirable vegetation. They have gained a high degree of commercial success because it has been shown that such control can increase crop yield and reduce harvesting costs.

Herbicidal effectiveness is dependent upon several variables. One of these is the time or growth related method of application. The most popular methods of application include: pre-plant incorporation into the soil; pre-emergence surface treatment of seeded soil; and post-emergence treatment of the plant and soil.

The most important determinant of herbicidal effectiveness is the susceptibility of the target weed pest. Certain herbicidal compounds are phytotoxic to some weed species but not to others.

The manufacturer of the herbicide recommends a range of rates and concentrations calculated to maximize weed control. The range of rates varies from approximately 0.01 to 50 pounds per acre (lb/A) (0.0112 to 56 kilograms per hectare (k/ha)), usually from 0.1 to 25 lb/A (0.112 to 28 k/ha). The actual amount used depends upon several considerations including particular weed susceptibility and overall cost limitations.

NEED FOR HERBICIDAL ANTIDOTES

Unfortunately, few herbicides are selective exclusively of weed species. Many are toxic to both weeds and the intended crop beneficiary. Therefore, a particular herbicide's use may be proscribed by its injurious effect on the cultivated crop even though it may otherwise provide excellent control of weeds plaguing that crop.

To preserve the beneficial aspects of herbicide use and to mitigate crop damage, many herbicidal antidotes have been prepared. These antidotes reduce or eliminate damage to the crop without substantially impairing the ameliorative effect of the herbicide. See U.S. Pat. No. 4,021,224 and Belgian Pat. No. 846,894.

Although several explanatory theories have been advanced, the precise mechanism by which an antidote reduces herbicidal crop injury while retaining weed injury has not been conclusively established. An antidote compound may in fact be a remedy, interferent, protectant, or antagonist. As used herein, "antidote" describes a compound which has the effect of establishing herbicidal selectivity.

DESCRIPTION OF THE INVENTION

Urea type herbicides have shown utility in the control of a wide variety of weeds plaguing numerous crops, such as cotton, sugarcane, pineapple, grapes, etc. However, the ureas have previously caused injury to soybeans.

It has been discovered that the tolerance of soybeans to urea-type herbicides can be increased by the use of an antidotally effective amount of a N-(benzenesulfonyl) carbamate compound of the formula

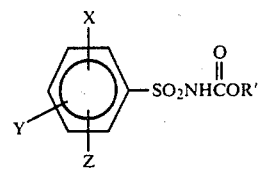

in which

X and Y are independently selected from the group consisting of hydrogen and methyl;

Z is selected from the group consisting of hydrogen, methyl, chloro, and trifluoromethyl; and R' is selected from the group consisting of 1-4 carbon alkyl, 1-4 carbon haloalkyl, preferably trifluoroethyl, 3-6 carbon alkenyl, 3-6 carbon haloalkenyl, where halo is preferably chloro, 3-6 carbon alkynyl, cyanoethylthioethyl, 2-6 carbon alkoxyalkyl, diethylhydroxylamine, acetoxime, methylthioacetimidate, substituted phenyl, preferably chlorosubstituted phenyl, substituted benzyl, preferably chlorosubstituted benzyl, and sulfolane.

This invention embodies a two-part herbicidal system comprising (a) an herbicidally effective amount of an urea of the formula

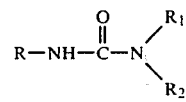

in which

R is selected from the group consisting of phenyl and substituted phenyl wherein the substituents are preferably chloro and acylamido;

$R_1$ is selected from the group consisting of hydrogen and 1-4 carbon alkyl; and $R_2$ is selected from the group consisting of 1-4 carbon alkyl and 1-4 carbon alkoxy; and (b) an antidotally effective amount of a N-(benzenesulfonyl) carbamate of the formula.

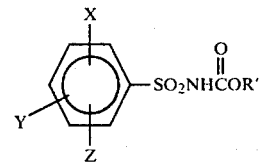

in which

X and Y are independently selected from the group consisting of hydrogen and methyl;

Z is selected from the group consisting of hydrogen, methyl, chloro, and trifluoromethyl; and R' is selected from the group consisting of 1-4 carbon alkyl, 1-4 carbon haloalkyl, preferably trifluoroethyl, 3-6 carbon alkenyl, 3-6 carbon haloalkenyl, wheere halo is preferably chloro, 3-6 carbon alkynyl, cyanoethylthioethyl, 3-6 carbon alkoxyalkyl, diethylhydroxylamine, acetoxime, methylthioacetimidate, substituted phenyl, preferably chlorosubstituted phenyl, substituted benzyl, preferably chlorosubstituted benzyl, and sulfolane.

This herbicidal system is particularly effective for the control of watergrass (*Echinochloa crusgalli*), Johnsongrass (*Sorghum halepense*) mustard (*Brassica juncea*), and curly dock (*Rumex crispus*).

The present invention includes the method of selectively controlling undesirable vegetation in the presence of soybeans which comprises adding to the soil (a) an herbicidally effective amount of an urea of the formula

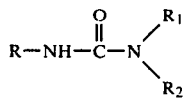

in which

R is selected from the group consisting of phenyl and substituted phenyl wherein the substituents are preferably chloro and acylamido;

$R_1$ is selected from the group consisting of hydrogen and 1-4 carbon alkyl; and $R_2$ is selected from the group consisting of 1-4 carbon alkyl and 1-4 carbon alkoxy; and (b) an antidotally effective amount of a N-(benzenesulfonyl) carbamate of the formula

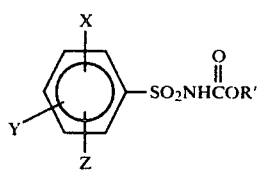

in which

X and Y are independently selected from the group consisting of hydrogen and methyl;

Z is selected from the group consisting of hydrogen, methyl, chloro, and trifluoromethyl; and R' is selected from the group consisting of 1-4 carbon alkyl, 1-4 carbon haloalkyl, preferably trifluoroethyl, 3-6 carbon alkenyl, 3-6 carbon haloalkenyl, where halo is preferably chloro, 3-6 carbon alkynyl, cyanoethylthioethyl, 2-6 carbon alkoxyalkyl, diethylhydroxylamine, acetoxime, methylthioacetimidate, substituted phenyl, preferably chloro-substituted phenyl, substituted benzyl, preferably chloro-substituted benzyl, and sulfolane.

The antidote may be combined with the herbicide in a tank mix by pre-plant incorporation (PPI). It may be applied by the in-furrow (IF) surface spray of seeds and soil before the seeds are covered with soil. It may be applied by seed treatment (ST). It may also be applied by pre-emergence (PES) methods of application which consist of spraying soil-covered seeds after planting.

This invention also includes soil treated with the herbicidal system comprised of an urea herbicide and a compound of the formula

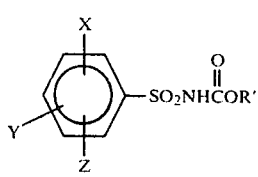

in which

X and Y are independently selected from the group consisting of hydrogen and methyl;

Z is selected from the group consisting of hydrogen, methyl, chloro, and trifluoromethyl; and R' is selected from the group consisting of 1-4 carbon alkyl, 1-4 carbon haloalkyl, preferably trifluoroethyl, 3-6 carbon alkenyl, 3-6 carbon haloalkenyl, where halo is preferably chloro, 3-6 carbon alkynyl, cyanoethylthioethyl, 3-6 carbon alkoxyalkyl, diethylhydroxylamine, acetoxime, methylthioacetimidate, substituted phenyl, preferably chlorosubstituted phenyl, substituted benzyl, preferably chlorosubstituted benzyl, and sulfolane.

PREPARATION

Any suitable urea-type herbicide may be used as part of the herbicidal composition of this invention. The herbicides tested were 3-(3', 4'-dichlorophenyl)-1,1-dimethylurea and 1(m-t-butylacetamidophenyl)3-methyl-3-methoxy urea. Each may be prepared by the procedures respectively described in U.S. Pat. Nos. 2,655,455 and 3,816,498.

The antidote compounds of this invention can be prepared by several different procedures depending upon the starting materials. Their general preparation is described in Belgium Pat. No. 846,894.

One method for preparing N-benzenesulfonyl alkyl carbamates is the reaction of an appropriate benzenesulfonamide with an alkyl chloroformate in the presence of an acid acceptor, such as potassium carbonate. A solvent is normally employed to facilitate the reaction and aid in the work-up of the product. After filtration, extraction and drying, the product can be purified further by trituration with hexane, or recyrstallization from a suitable solvent. Structures are usually confirmed by infrared, nuclear magnetic resonance or mass spectroscopy.

The following examples illustrate the preparation of specific compounds typical of this invention. (The compound numbers correspond to those appearing in Tables I and IV).

EXAMPLE 1

(Compound No. 7)

Preparation of N-(benzenesulfonyl)-2,2,2-trifluoroethyl carbamate

A solution of 3.0 grams (g) (0.03 mole) of 2,2,2-trifluoroethanol in 25 milliliters (ml) benzene, and one drop each of triethylamine and dibutyltin dilaurate was prepared. Benzenesulfonyl isocyanate (5.5 g or 0.03 mole) in 25 ml of benzene was added to the solution while the temperature was maintained below 30° C. The mixture was stirred overnight at room temperature and for ½ hour at 40°–45° C. The solvent was removed by vacuum evaporation. The product was triturated with hexane and dried, yielding 8.0 g of N-(benzenesulfonyl)-2,2,2-trifluoroethyl carbamate (m.p. 93°–95° C.). Structure was confirmed by infrared spectroscopy (IR).

EXAMPLE 2

(Compound No. 10)

Preparation of N-(m-chlorobenzenesulfonyl)-2,2,2-trifluoroethyl carbamate

The reaction was identical to that of Example 1 with the substitution of 4.4 g (0.02 mole) m-chlorobenzene sulfonyl isocyanate which was reacted with 2.2 g (0.022 mole) trifluoroethanol. The product (m.p. 108°–110° C.) was confirmed by IR.

EXAMPLE 3

(Compound No. 16)

Preparation of N-(m-trifluoromethylbenzenesulfonyl) allyl carbamate

A solution was prepared containing 0.715 g (0.0123 mole) of allyl alcohol, 20 ml of benzene and one drop each of triethylamine and dibutyltin dilaurate. A second solution of 3.1 g (0.0123 mole) m-trifluoromethylbenzenesulfonyl isocyanate in 20 ml benzene was added to the first solution. The temperature of the mixture was allowed to rise to 35° C. The solution was stirred for 3 hours at room temperature followed by stirring for ½ hour at 40°–45° C.

After removal of the solvent by vacuum evaporation, the residual oil was slowly crystallized. The product was triturated and dried, yielding 3.3 g (87%) of N-(m-trifluoromethylbenzenesulfonyl)-allyl carbamate (m.p. 66°–70° C.). The structure was confirmed by IR.

EXAMPLE 4

(Compound No. 28)

Preparation of N-(p-toluenesulfonyl)-2-(2'-cyanoethyl) thioethyl carbamate

The reaction was carried out in the same manner as for Example 3 with the second solution containing 2.97 g (0.015 mole) of p-toluenesulfonyl isocyanate added to the first solution of 1.98 g (0.015 mole) of 2-(2-cyanoethylthio)-ethanol in 20 ml of benzene.

The yield was 5.3 g (100% of a viscous liquid product) ($n_D^{30}$ 1.5482). Structure was confirmed by nuclear magnetic resonance (NMR).

EXAMPLE 5

(Compound No. 34)

Preparation of N-(p-chlorobenzenesulfonyl)-p-chlorobenzyl carbamate

The reaction was carried out in the same manner as in Examples 3 and 4 with the second solution containing 5.9 g (0.03 mole) p-chlorobenzenesulfonyl isocyanate added to the first solution which contained 4.3 g (0.03 mole) p-chlorobenzyl alcohol. The yield was 7.5 g (74%) of N-(p-chlorobenzenesulfonyl)-p-chlorobenzyl carbamate (m.p. 138°–139° C.). Structure was confirmed by IR.

Table I contains antidote compounds, representative of those used in the herbicidal compositions of this invention, prepared according to the procedures described in the Examples.

TABLE I

N—(BENZENESULFONYL) CARBAMATES

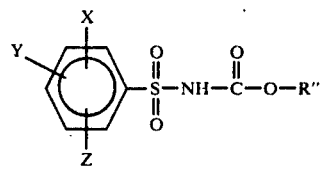

| Cmpd. No. | X | Y | Z | R' | Chemical Name | Physical Constant |
|---|---|---|---|---|---|---|
| 1 | H | H | 4-Cl | $CH_3$ | N—(p-chlorobenzenesulfonyl) methyl carbamate | m.p. 127–130° C. |
| 2 | 2-$CH_3$ | 4-$CH_3$ | 6-$CH_3$ | $C_2H_5$ | N—(mesitylenesulfonyl) ethyl carbamate | m.p. 159–160° C. |
| 3 | H | H | 4-Cl | $C_2H_5$ | N—(p-chlorobenzenesulfonyl) ethyl carbamate | m.p. 85–90° C. |
| 4 | H | H | 3-Cl | $C_2H_5$ | N—(m-chlorobenzenesulfonyl) ethyl carbamate | $n_D^{30}$ 1.5155 |
| 5 | H | H | 3-$CF_3$ | $C_2H_5$ | N—(m-trifluoromethylbenzenesulfonyl) ethyl carbamate | m.p. 59–63° C. |
| 6 | H | H | H | $CH_2CCl_3$ | N—(benzenesulfonyl) 2,2,2-trichloroethyl carbamate | m.p. 121–122° C. |
| 7 | H | H | H | $CH_2CF_3$ | N—(benzenesulfonyl) 2,2,2-trifluoroethyl carbamate | m.p. 93–95° C. |
| 8 | H | H | 4-$CH_3$ | $CH_2CF_3$ | N—(p-toluenesulfonyl) 2,2,2-trifluoroethyl carbamate | m.p. 120–125° C. |
| 9 | H | H | 4-Cl | $CH_2CF_3$ | N—(p-chlorobenzenesulfonyl) 2,2,2-trifluoroethyl carbamate | m.p. 142–145° C. |
| 10 | H | H | 3-Cl | $CH_2CF_3$ | N—(m-chlorobenzenesulfonyl) 2,2,2-trifluoroethyl carbamate | m.p. 108–110° C. |
| 11 | 2-$CH_3$ | 4-$CH_3$ | 6-$CH_3$ | $CH_2CF_3$ | N—(mesitylenesulfonyl) 2,2,2-trifluoroethyl carbamate | m.p. 159–162° C. |
| 12 | H | H | H | $CH_2CH=CH_2$ | N—(benzenesulfonyl) allyl carbamate | $n_D^{30}$ 1.5175 |
| 13 | H | H | 4-$CH_3$ | $CH_2CH=CH_2$ | N—(p-toluenesulfonyl) allyl carbamate | $n_D^{30}$ 1.5375 |
| 14 | H | H | 4-Cl | $CH_2CH=CH_2$ | N—(p-chlorobenzenesulfonyl) allyl carbamate | $n_D^{30}$ 1.5262 |
| 15 | H | H | 3-Cl | $CH_2CH=CH_2$ | N—(m-chlorobenzenesulfonyl) allyl carbamate | m.p. 58–61° C. |
| 16 | H | H | 3-$CF_3$ | $CH_2CH=CH_2$ | N—(m-trifluoromethylbenzenesulfonyl) allyl carbamate | m.p. 66–70° C. |
| 17 | H | H | H | $CH_2CCl=CH_2$ | N—(benzenesulfonyl) 2-chloroallyl carbamate | viscous semi-solid |

TABLE I-continued
N—(BENZENESULFONYL) CARBAMATES

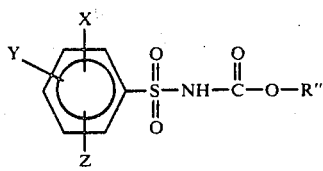

| Cmpd. No. | X | Y | Z | R' | Chemical Name | Physical Constant |
|---|---|---|---|---|---|---|
| 18 | H | H | 4-CH$_3$ | CH$_2$CCl=CH$_2$ | N—(p-toluenesulfonyl) 2-chloroallyl carbamate | $n_D^{30}$ 1.5340 |
| 19 | H | H | 4-Cl | CH$_2$CCl=CH$_2$ | N—(p-chlorobenzenesulfonyl) 2-chloroallyl carbamate | m.p. 89–93° C. |
| 20 | H | H | H | CH$_2$C≡CH | N—(benzenesulfonyl) propargyl carbamate | m.p. 78–80° C. |
| 21 | H | H | 4-CH$_3$ | CH$_2$C≡CH | N—(p-toluenesulfonyl) propargyl carbamate | $n_D^{30}$ 1.5384 |
| 22 | H | H | 4-Cl | CH$_2$C≡CH | N—(p-chlorobenzenesulfonyl) propargyl carbamate | m.p. 106–108° C. |
| 23 | H | H | 3-Cl | CH$_2$C≡CH | N—(m-chlorobenzenesulfonyl) propargyl carbamate | m.p. 73–76° C. |
| 24 | H | H | 3-CF$_3$ | CH$_2$C≡CH | N—(m-trifluoromethylbenzenesulfonyl) propargyl carbamate | m.p. 76–77° C. |
| 25 | 2-CH$_3$ | 4-CH$_3$ | 6-CH$_3$ | CH$_2$C≡CH | N—(mesitylenesulfonyl) propargyl carbamate | m.p. 150–151° C. |
| 26 | H | H | 4-CH$_3$ | CH$_2$C≡CCH$_3$ | N—(p-toluenesulfonyl) 2-butyn-1-yl carbamate | m.p. 85–90° C. |
| 27 | H | H | 4-Cl | CH$_2$C≡CCH$_3$ | N—(p-chlorobenzenesulfonyl) 2-butyn-1-yl carbamate | m.p. 141–142° C. |
| 28 | H | H | 4-CH$_3$ | (CH$_2$)$_2$S(CH$_2$)$_2$CN | N—(p-toluenesulfonyl) 2-(2'-cyanoethyl) thioethyl carbamate | $n_D^{30}$ 1.5482 |
| 29 | H | H | 4-Cl | CH$_2$CH$_2$OC$_2$H$_5$ | N—(p-chlorobenzenesulfonyl) 2-ethoxyethyl carbamate | semi-solid |
| 30 | H | H | 4-CH$_3$ | NC$_2$H$_5$ | N,N—diethylhydroxylamine-N'—(p-toluenesulfonyl) carbamate | semi-solid |
| 31 | H | H | 4-Cl | N=C(CH$_3$)$_2$ | N—(p-chlorobenzenesulfonyl) acetone oxime carbamate | m.p. 161–162° C. |
| 32 | H | H | 4-Cl | N=C(CH$_3$)(SCH$_3$) | Methyl-N—[(4-chlorobenzenesulfonylcarbamoyl)oxy] thioacetimidate | m.p. 125–128° C. |
| 33 | H | H | 4-Cl | C$_6$H$_4$-Cl | N—(p-chlorobenzenesulfonyl) p-chlorophenyl carbamate | m.p. 159–160° C. |
| 34 | H | H | 4-Cl | CH$_2$-C$_6$H$_4$-Cl | N—(p-chlorobenzenesulfonyl) p-chlorobenzylcarbamate | m.p. 138–139° C. |
| 35 | H | H | 4-Cl | (5-methyl-1,3-dioxan-5-yl)methyl | N—(p-chlorobenzenesulfonyl) carbamate of 5-hydroxymethyl-5-methyl-1,3-dioxane | viscous semi-solid |
| 36 | H | H | 4-CH$_3$ | 3-sulfolanyl | N—(p-toluenesulfonyl) carbamate of 3-hydroxy sulfolane | semi-solid |

TESTING

Stock solutions of 3-(3',4'-dichlorophenyl)-1,1-dimethylurea (Herbicide A) was prepared by dissolving the requisite amount of the herbicide in water. Stock solutions of 1-(m-t-butylacetamidophenyl)-3-methyl-3-methoxyurea (Herbicide B) were prepared by dissolving the herbicide in acetone.

Stock solutions of each antidote compound were prepared by dissolving the requisite amount in acetone. The herbicide and antidote compositions and their equivalent rates of application appear in Tables II and III.

TABLE II

| Herbicidal Stock Solutions | | | |
|---|---|---|---|
| Composition | | Application | |
| Herbicide A (mg) | Water (ml) | ml soln | ~ lb/A |
| 61 | 125 | 5.0 | 0.5 PPI* |
| 400 | 200 | 2.5 | 1.0 PPI |
| 400 | 200 | 5.0 | 2.0 PPI |

TABLE II-continued

| Herbicidal Stock Solutions | | | |
|---|---|---|---|
| Composition | | Application | |
| 150 | 50 | 5.0 | 3.0 PPI |
| 7500 | 1000 | Linear spray | 4.0 PES |
| Herbicide B (mg) | Acetone (ml) | ml soln | ~ lb/A |
| 75 | 200 | Linear spray | 0.25 PES |
| 24 | 125 | 5.0 | 0.25 PPI |
| 150 | 200 | Linear spray | 0.50 PES |
| 40 | 50 | 5.0 | 1.00 PPI |

*See Table IV for explanation of methods of application.

TABLE III

| Antidote Stock Solutions | | | |
|---|---|---|---|
| Antidote: N—(benzenesulfonyl) carbamate | | | |
| Composition | | Application | |
| Antidote (mg) | Acetone (ml) | ml soln | ~ lb/A |
| 95 | 15 | 1.5 | 5.0 IF |
| 39 | 10 | 1.0 | 1.00 PPI |
| 40 | 20 | 4.0 | 2.00 PPI |
| 39 | 10 | 5.0 | 5.00 PPI |
| 95 | 15 | 3.0 | 5.00 PES |
| 250 | 2.5 | .5/10 grams seed | 0.5% ST |

All of the soil used in the tests described herein was loamy sand soil treated with 50 parts per million (ppm) each of a commercially available fungicide, cis-N[(trichloromethyl) thio]-4-cyclohexene-1,2-dicarboximide, and an 18-18-18 fertilizer which contains 18% by weight equivalent each of nitrogen, phosphorus pentoxide, and potassium oxide.

For the pre-plant incorporation (PPI) method, the herbicide and the antidote of each test group were incorporated into sandy loam soil as a tank mix using a five gallon rotary mixer. Control flats used for injury rating comparisons contained only the herbicide treated soil.

For in-furrow (IF) antidote applications, planting flats were filled with sandy loam soil treated by PPI of the herbicide. A one pint sample of soil removed from each flat was retained to cover the seeds after treatment. After leveling and furrowing the soil, seeds of the crop or weed species were planted ½ inch deep. Each flat was divided in half by a wooden barrier. A stock solution of the antidote wwas atomized directly onto the exposed seeds and soil in the open furrows of one-half of the flat. The seeds were then covered with the previously removed soil. The untreated sections of the flats containing identical herbicide concentrations was compared for observed differences which would indicate lateral movement of the antidote through the soil.

Pre-emergence surface application (PES) of the herbicide and antidote consists of placing the seeded flat on a linear spray table calibrated to deliver an equivalent of 80 gallons per acre (749.6 liters per hectare). Where both herbicide and antidote were applied by this method, the stock solutions were combined prior to application.

Seed treatment (ST) consists of shaking in a suitable container 10 g of seed and 0.5 ml of antidote stock solution.

The flats were placed on greenhouse benches where temperature was maintained between 70° and 90° F. (21.11° to 32.22° C.). The soil was watered by sprinkling as needed to assure good plant growth.

The effectiveness of the antidote and the herbicidal composition was determined by comparing the crop and weed species treated at each level of concentration to untreated species.

Injury ratings, taken four weeks after treatment, are reported in Table IV.

TABLE IV

| | | | | | | | | | | | | | |
|---|---|---|---|---|---|---|---|---|---|---|---|---|---|
| N—(BENZENESULFONYL) CARBAMATES ANTIDOTAL AND HERBICIDAL EFFECTIVENESS | | | | | | | | | | | | | |
| | Antidote | | Herbicide | | % Injury | | | | | | | | |
| Cmpd. | Application | | Application | | Soybeans | | Watergrass | | Mustard | | Curly Dock | | Johnsongrass | |
| No. | Rate | Method | Rate | Method | U | T | U | T | U | T | U | T | U | T |
| 1 | 0.50 | PPI | A 0.50 | PPI | 100 | 0 | | | 100 | — | 100 | 70 | | |
| | 1.00 | PPI | A 0.50 | PPI | 100 | 0 | | | 100 | 60 | 100 | 60 | | |
| | 2.00 | PPI | A 0.50 | PPI | 100 | 0 | | | 100 | — | 100 | 70 | | |
| | 0.25 | PPI | A 1.00 | PPI | 100 | — | | | 100 | — | 100 | — | | |
| | 0.50 | PPI | A 1.00 | PPI | 100 | — | | | 100 | — | 100 | — | | |
| | 1.00 | PPI | A 1.00 | PPI | 100 | — | | | 100 | — | 100 | — | | |
| | 2.00 | PPI | A 1.00 | PPI | 100 | — | | | 100 | — | 100 | — | | |
| | 0.25 | PPI | A 2.00 | PPI | 100 | — | | | 100 | — | 100 | — | | |
| | 0.50 | PPI | A 2.00 | PPI | 100 | — | | | 100 | — | 100 | — | | |
| | 1.00 | PPI | A 2.00 | PPI | 100 | — | | | 100 | — | 100 | — | | |
| | 2.00 | PPI | A 2.00 | PPI | 100 | — | | | 100 | — | 100 | — | | |
| | 0.50 | PPI | B 0.25 | PPI | 100 | — | | | 100 | — | 100 | 80 | | |
| | 1.00 | PPI | B 0.25 | PPI | 100 | — | | | 100 | — | 100 | 60 | | |
| | 2.00 | PPI | B 0.25 | PPI | 100 | 40 | | | 100 | — | 100 | 70 | | |
| 2 | 5.00 | IF | A 0.50 | PPI | 100 | — | 100 | — | | | | | 100 | — |
| | 5.00 | IF | A 0.50 | PES | 100 | — | 100 | — | | | | | 100 | — |
| | 5.00 | PPI | A 0.50 | PPI | 100 | — | 100 | — | | | | | 100 | — |
| | 5.00 | PES | A 0.50 | PES | 90 | — | 100 | — | | | | | 100 | — |
| | 0.5% | ST | A 0.50 | PPI | 90 | — | 100 | — | | | | | 90 | — |
| | 0.5% | ST | A 0.50 | PES | 90 | 70 | 100 | — | | | | | 100 | — |
| 3 | 5.00 | PPI | A 0.50 | PPI | 80 | 30 | | | 100 | — | 100 | — | | |
| | 5.00 | PPI | A 3.00 | PPI | | | 100 | — | 100 | — | | | | |
| | 0.50 | PPI | A 0.50 | PPI | 100 | 70 | | | 100 | — | 100 | — | | |
| | 1.00 | PPI | A 0.50 | PPI | 100 | 70 | | | 100 | — | 100 | — | | |
| | 0.50 | PPI | B 0.25 | PPI | 100 | — | | | 100 | — | 100 | — | | |
| | 1.00 | PPI | B 0.25 | PPI | 100 | — | | | 100 | — | 100 | 60 | | |
| | 2.00 | PPI | B 0.25 | PPI | 100 | 60 | | | 100 | — | 100 | 50 | | |
| | 5.00 | IF | A 0.50 | PPI | 100 | 90 | 100 | — | | | | | 100 | — |
| | 5.00 | IF | A 0.50 | PES | 100 | 70 | 100 | — | | | | | 100 | — |
| | 5.00 | PPI | A 0.50 | PPI | 100 | 80 | 100 | — | | | | | 100 | — |

TABLE IV-continued
N—(BENZENESULFONYL) CARBAMATES
ANTIDOTAL AND HERBICIDAL EFFECTIVENESS

| Cmpd. No. | Antidote Application Rate | Antidote Application Method | Herbicide Application Rate | Herbicide Application Method | Soybeans U | Soybeans T | Watergrass U | Watergrass T | Mustard U | Mustard T | Curly Dock U | Curly Dock T | Johnsongrass U | Johnsongrass T |
|---|---|---|---|---|---|---|---|---|---|---|---|---|---|---|
| | 5.00 | PES | A 0.50 | PES | 90 | 80 | 100 | — | | | | | 100 | — |
| | 0.5% | ST | A 0.50 | PPI | 90 | 70 | 100 | — | | | | | 90 | — |
| | 0.5% | ST | A 0.50 | PES | 90 | 40 | 100 | — | | | | | 100 | — |
| 4 | 5.00 | IF | A 0.50 | PPI | 100 | 80 | 100 | — | | | | | 100 | — |
| | 5.00 | IF | A 0.50 | PES | 100 | 75 | 100 | — | | | | | 100 | — |
| | 5.00 | PPI | A 0.50 | PPI | 100 | 70 | 100 | — | | | | | 100 | — |
| | 5.00 | PES | A 0.50 | PES | 90 | 60 | 100 | — | | | | | 100 | — |
| | 0.5% | ST | A 0.50 | PPI | 90 | 80 | 100 | — | | | | | 90 | — |
| | 0.5% | ST | A 0.50 | PES | 90 | — | 100 | — | | | | | 100 | — |
| 5 | 5.00 | IF | A 0.50 | PPI | 100 | 90 | 100 | — | | | | | 100 | — |
| | 5.00 | IF | A 0.50 | PES | 100 | 70 | 100 | — | | | | | 100 | — |
| | 5.00 | PPI | A 0.50 | PPI | 100 | — | 100 | — | | | | | 100 | — |
| | 5.00 | PES | A 0.50 | PES | 90 | — | 100 | — | | | | | 100 | — |
| | 0.5% | ST | A 0.50 | PPI | 90 | — | 100 | — | | | | | 90 | — |
| | 0.5% | ST | A 0.50 | PES | 90 | 80 | 100 | — | | | | | 100 | — |
| 6 | 0.50 | PPI | A 0.50 | PPI | 100 | 70 | | | 100 | — | 100 | — | | |
| | 1.00 | PPI | A 0.50 | PPI | 100 | — | | | 100 | — | 100 | — | | |
| | 2.00 | PPI | A 0.50 | PPI | 100 | — | | | 100 | — | 100 | — | | |
| | 0.50 | PPI | B 0.25 | PPI | 100 | 70 | | | 100 | — | 100 | — | | |
| | 1.00 | PPI | B 0.25 | PPI | 100 | — | | | 100 | — | 100 | — | | |
| | 2.00 | PPI | B 0.25 | PPI | 100 | — | | | 100 | — | 100 | — | | |
| 7 | 0.50 | PPI | A 0.50 | PPI | 100 | 0 | | | 100 | 50 | 100 | 50 | | |
| | 1.00 | PPI | A 0.50 | PPI | 100 | 0 | | | 100 | 50 | 100 | 50 | | |
| | 2.00 | PPI | A 0.50 | PPI | 100 | 0 | | | 100 | 50 | 100 | 50 | | |
| | 0.25 | PPI | A 1.00 | PPI | 100 | — | | | 100 | — | 100 | — | | |
| | 0.50 | PPI | A 1.00 | PPI | 100 | — | | | 100 | — | 100 | — | | |
| | 1.00 | PPI | A 1.00 | PPI | 100 | — | | | 100 | — | 100 | — | | |
| | 2.00 | PPI | A 1.00 | PPI | 100 | — | | | 100 | — | 100 | — | | |
| | 0.25 | PPI | A 2.00 | PPI | 100 | — | | | 100 | — | 100 | — | | |
| | 0.50 | PPI | A 2.00 | PPI | 100 | — | | | 100 | — | 100 | — | | |
| | 1.00 | PPI | A 2.00 | PPI | 100 | — | | | 100 | — | 100 | — | | |
| | 2.00 | PPI | A 2.00 | PPI | 100 | — | | | 100 | — | 100 | — | | |
| | 0.50 | PPI | B 0.25 | PPI | 100 | — | | | 100 | — | 100 | — | | |
| | 1.00 | PPI | B 0.25 | PPI | 100 | — | | | 100 | — | 100 | — | | |
| | 2.00 | PPI | B 0.25 | PPI | 100 | — | | | 100 | — | 100 | — | | |
| | 5.00 | IF | A 0.50 | PPI | 100 | — | 100 | — | | | | | 100 | — |
| | 5.00 | IF | A 0.50 | PES | 100 | — | 100 | — | | | | | 100 | — |
| | 5.00 | PPI | A 0.50 | PPI | 100 | — | 100 | — | | | | | 100 | — |
| | 5.00 | PES | A 0.50 | PES | 90 | — | 100 | — | | | | | 100 | — |
| | 0.5% | ST | A 0.50 | PPI | 90 | — | 100 | — | | | | | 90 | — |
| | 0.5% | ST | A 0.50 | PES | 90 | — | 100 | — | | | | | 100 | — |
| 8 | 5.00 | IF | A 0.50 | PPI | 100 | — | 100 | — | | | | | 100 | — |
| | 5.00 | IF | A 0.50 | PES | 100 | — | 100 | — | | | | | 100 | — |
| | 5.00 | PPI | A 0.50 | PPI | 100 | — | 100 | — | | | | | 100 | — |
| | 5.00 | PES | A 0.50 | PES | 90 | — | 100 | — | | | | | 100 | — |
| | 0.5% | ST | A 0.50 | PPI | 90 | — | 100 | — | | | | | 90 | — |
| | 0.5% | ST | A 0.50 | PES | 90 | 65 | 100 | — | | | | | 100 | — |
| 9 | 5.00 | IF | A 0.50 | PPI | 100 | — | 100 | — | | | | | 100 | — |
| | 5.00 | IF | A 0.50 | PES | 100 | — | 100 | — | | | | | 100 | — |
| | 5.00 | PPI | A 0.50 | PPI | 100 | — | 100 | — | | | | | 100 | — |
| | 5.00 | PES | A 0.50 | PES | 90 | — | 100 | — | | | | | 100 | — |
| | 0.5% | ST | A 0.50 | PPI | 90 | — | 100 | — | | | | | 90 | — |
| | 0.5% | ST | A 0.50 | PES | 90 | 55 | 100 | — | | | | | 100 | — |
| 10 | 5.00 | IF | A 0.50 | PPI | 100 | — | 100 | — | | | | | 100 | — |
| | 5.00 | IF | A 0.50 | PES | 100 | 50 | 100 | — | | | | | 100 | — |
| | 5.00 | PPI | A 0.50 | PPI | 100 | — | 100 | — | | | | | 100 | — |
| | 5.00 | PES | A 0.50 | PES | 90 | — | 100 | — | | | | | 100 | — |
| | 0.5% | ST | A 0.50 | PPI | 90 | 80 | 100 | — | | | | | 90 | — |
| | 0.5% | ST | A 0.50 | PES | 90 | 80 | 100 | — | | | | | 100 | — |
| | 0.50 | PPI | A 0.50 | PPI | 100 | — | | | 100 | — | 100 | — | | |
| | 1.00 | PPI | A 0.50 | PPI | 100 | — | | | 100 | — | 100 | — | | |
| | 2.00 | PPI | A 0.50 | PPI | 100 | 50 | | | 100 | — | 100 | — | | |
| | 0.50 | PPI | B 0.25 | PPI | 100 | — | | | 100 | — | 100 | — | | |
| | 1.00 | PPI | B 0.25 | PPI | 100 | — | | | 100 | — | 100 | — | | |
| | 2.00 | PPI | B 0.25 | PPI | 100 | 50 | | | 100 | — | 100 | — | | |
| 11 | 5.00 | IF | A 0.50 | PPI | 100 | — | 100 | — | | | | | 100 | — |
| | 5.00 | IF | A 0.50 | PES | 100 | 75 | 100 | — | | | | | 100 | — |
| | 5.00 | PPI | A 0.50 | PPI | 100 | — | 100 | — | | | | | 100 | — |
| | 5.00 | PES | A 0.50 | PES | 90 | — | 100 | — | | | | | 100 | — |
| | 0.5% | ST | A 0.50 | PPI | 90 | — | 100 | — | | | | | 90 | — |
| | 0.5% | ST | A 0.50 | PES | 90 | — | 100 | — | | | | | 100 | — |
| 12 | 5.00 | IF | A 0.50 | PPI | 100 | 70 | 100 | — | | | | | 100 | — |
| | 5.00 | IF | A 0.50 | PES | 100 | — | 100 | — | | | | | 100 | — |
| | 5.00 | PPI | A 0.50 | PPI | 100 | — | 100 | — | | | | | 100 | — |
| | 5.00 | PES | A 0.50 | PES | 90 | — | 100 | — | | | | | 100 | — |
| | 0.5% | ST | A 0.50 | PPI | 90 | — | 100 | — | | | | | 90 | — |

TABLE IV-continued
N—(BENZENESULFONYL) CARBAMATES
ANTIDOTAL AND HERBICIDAL EFFECTIVENESS

| Cmpd. No. | Antidote Application Rate | Antidote Application Method | Herbicide Application Rate | Herbicide Application Method | Soybeans U | Soybeans T | Watergrass U | Watergrass T | Mustard U | Mustard T | Curly Dock U | Curly Dock T | Johnsongrass U | Johnsongrass T |
|---|---|---|---|---|---|---|---|---|---|---|---|---|---|---|
| | 0.5% | ST | A 0.50 | PES | 90 | — | 100 | — | | | | | 100 | — |
| 14 | 5.00 | IF | A 0.50 | PPI | 100 | — | 100 | — | | | | | 100 | — |
| | 5.00 | IF | A 0.50 | PES | 100 | 80 | 100 | — | | | | | 100 | — |
| | 5.00 | PPI | A 0.50 | PPI | 100 | — | 100 | — | | | | | 100 | — |
| | 5.00 | PES | A 0.50 | PES | 90 | 60 | 100 | — | | | | | 100 | — |
| | 0.5% | ST | A 0.50 | PPI | 90 | — | 100 | — | | | | | 90 | — |
| | 0.5% | ST | A 0.50 | PES | 90 | 60 | 100 | — | | | | | 100 | — |
| 15 | 5.00 | IF | A 0.50 | PPI | 100 | — | 100 | — | | | | | 100 | — |
| | 5.00 | IF | A 0.50 | PES | 100 | 75 | 100 | — | | | | | 100 | — |
| | 5.00 | PPI | A 0.50 | PPI | 100 | — | 100 | — | | | | | 100 | — |
| | 5.00 | PES | A 0.50 | PES | 90 | — | 100 | — | | | | | 100 | — |
| | 0.5% | ST | A 0.50 | PPI | 90 | 80 | 100 | — | | | | | 100 | — |
| | 0.5% | ST | A 0.50 | PES | 90 | 40 | 100 | — | | | | | 100 | — |
| 16 | 5.00 | IF | A 0.50 | PPI | 100 | — | 100 | — | | | | | 100 | — |
| | 5.00 | IF | A 0.50 | PES | 100 | — | 100 | — | | | | | 100 | — |
| | 5.00 | PPI | A 0.50 | PPI | 100 | 65 | 100 | — | | | | | 100 | — |
| | 5.00 | PES | A 0.50 | PES | 90 | — | 100 | — | | | | | 100 | — |
| | 0.5% | ST | A 0.50 | PPI | 90 | — | 100 | — | | | | | 90 | — |
| | 0.5% | ST | A 0.50 | PES | 90 | 35 | 100 | — | | | | | 100 | — |
| 17 | 5.00 | IF | A 0.50 | PPI | 100 | — | 100 | — | | | | | 100 | — |
| | 5.00 | IF | A 0.50 | PES | 100 | — | 100 | — | | | | | 100 | — |
| | 5.00 | PPI | A 0.50 | PPI | 100 | 80 | 100 | — | | | | | 100 | — |
| | 5.00 | PES | A 0.50 | PES | 90 | — | 100 | — | | | | | 100 | — |
| | 0.5% | ST | A 0.50 | PPI | 90 | — | 100 | — | | | | | 90 | — |
| | 0.5% | ST | A 0.50 | PES | 90 | 50 | 100 | — | | | | | 100 | — |
| 18 | 5.00 | IF | A 0.50 | PPI | 100 | — | 100 | — | | | | | 100 | — |
| | 5.00 | IF | A 0.50 | PES | 100 | — | 100 | — | | | | | 100 | — |
| | 5.00 | PPI | A 0.50 | PPI | 100 | — | 100 | — | | | | | 100 | — |
| | 5.00 | PES | A 0.50 | PES | 90 | — | 100 | — | | | | | 100 | — |
| | 0.5% | ST | A 0.50 | PPI | 90 | — | 100 | — | | | | | 90 | — |
| | 0.5% | ST | A 0.50 | PES | 90 | 55 | 100 | — | | | | | 100 | — |
| 19 | 5.00 | IF | A 0.50 | PPI | 100 | — | 100 | — | | | | | 100 | — |
| | 5.00 | IF | A 0.50 | PES | 100 | — | 100 | — | | | | | 100 | — |
| | 5.00 | PPI | A 0.50 | PPI | 100 | — | 100 | — | | | | | 100 | — |
| | 5.00 | PES | A 0.50 | PES | 90 | — | 100 | — | | | | | 100 | — |
| | 0.5% | ST | A 0.50 | PPI | 90 | — | 100 | — | | | | | 90 | — |
| | 0.5% | ST | A 0.50 | PES | 90 | 70 | 100 | — | | | | | 100 | — |
| 22 | 5.00 | IF | A 0.50 | PPI | 100 | — | 100 | — | | | | | 100 | — |
| | 5.00 | IF | A 0.50 | PES | 100 | — | 100 | — | | | | | 100 | — |
| | 5.00 | PPI | A 0.50 | PPI | 100 | — | 100 | — | | | | | 100 | — |
| | 5.00 | PES | A 0.50 | PES | 90 | — | 100 | — | | | | | 100 | — |
| | 0.5% | ST | A 0.50 | PPI | 90 | — | 100 | — | | | | | 90 | — |
| | 0.5% | ST | A 0.50 | PES | 90 | 50 | 100 | — | | | | | 100 | — |
| | 0.50 | PPI | A 0.50 | PPI | 100 | 0 | | | 100 | 50 | 100 | 50 | | |
| | 1.00 | PPI | A 0.50 | PPI | 100 | 0 | | | 100 | 50 | 100 | 50 | | |
| | 2.00 | PPI | A 0.50 | PPI | 100 | 0 | | | 100 | 50 | 100 | 50 | | |
| | 0.50 | PPI | A 1.00 | PPI | 100 | — | | | 100 | — | 100 | — | | |
| | 1.00 | PPI | A 1.00 | PPI | 100 | — | | | 100 | — | 100 | — | | |
| | 2.00 | PPI | A 1.00 | PPI | 100 | — | | | 100 | — | 100 | — | | |
| | 0.25 | PPI | A 2.00 | PPI | 100 | — | | | 100 | — | 100 | — | | |
| | 0.50 | PPI | A 2.00 | PPI | 100 | — | | | 100 | — | 100 | — | | |
| | 1.00 | PPI | A 2.00 | PPI | 100 | — | | | 100 | — | 100 | — | | |
| | 2.00 | PPI | A 2.00 | PPI | 100 | — | | | 100 | — | 100 | — | | |
| | 0.50 | PPI | B 0.25 | PPI | 10 | 50 | | | 100 | — | 100 | 50 | | |
| | 1.00 | PPI | B 0.25 | PPI | 100 | 60 | | | 100 | — | 100 | 60 | | |
| | 2.00 | PPI | B 0.25 | PPI | 100 | 80 | | | 100 | — | 100 | 50 | | |
| | 5.00 | IF | B 0.25 | PES | 100 | — | | | | | | | | |
| | 5.00 | IF | B 0.50 | PES | 100 | — | | | | | | | | |
| 23 | 5.00 | IF | A 0.50 | PPI | 100 | — | 100 | — | | | | | 100 | — |
| | 5.00 | IF | A 0.50 | PES | 100 | — | 100 | — | | | | | 100 | — |
| | 5.00 | PPI | A 0.50 | PPI | 100 | — | 100 | — | | | | | 100 | — |
| | 5.00 | PES | A 0.50 | PES | 90 | 80 | 100 | — | | | | | 100 | — |
| | 0.5% | ST | A 0.50 | PPI | 90 | 80 | 100 | — | | | | | 90 | — |
| | 0.5% | ST | A 0.50 | PES | 90 | — | 100 | — | | | | | 100 | — |
| 24 | 5.00 | IF | A 0.50 | PPI | 100 | — | 100 | — | | | | | 100 | — |
| | 5.00 | IF | A 0.50 | PES | 100 | 40 | 100 | — | | | | | 100 | — |
| | 5.00 | PPI | A 0.50 | PPI | 100 | — | 100 | — | | | | | 100 | — |
| | 5.00 | PES | A 0.50 | PES | 90 | 80 | 100 | — | | | | | 100 | — |
| | 0.5% | ST | A 0.50 | PPI | 90 | 70 | 100 | — | | | | | 90 | — |
| | 0.5% | ST | A 0.50 | PES | 90 | 80 | 100 | — | | | | | 100 | — |
| 25 | 5.00 | IF | A 0.50 | PPI | 100 | — | 100 | — | | | | | 100 | — |
| | 5.00 | IF | A 0.50 | PES | 100 | — | 100 | — | | | | | 100 | — |
| | 5.00 | PPI | A 0.50 | PPI | 100 | — | 100 | — | | | | | 100 | — |
| | 5.00 | PES | A 0.50 | PES | 90 | — | 100 | — | | | | | 100 | — |
| | 0.5% | ST | A 0.50 | PPI | 90 | — | 100 | — | | | | | 90 | — |
| | 0.5% | ST | A 0.50 | PES | 90 | 70 | 100 | — | | | | | 100 | — |

TABLE IV-continued
N—(BENZENESULFONYL) CARBAMATES
ANTIDOTAL AND HERBICIDAL EFFECTIVENESS

| Cmpd. No. | Antidote Application Rate | Antidote Application Method | Herbicide Application Rate | Herbicide Application Method | Soybeans U | Soybeans T | Watergrass U | Watergrass T | Mustard U | Mustard T | Curly Dock U | Curly Dock T | Johnsongrass U | Johnsongrass T |
|---|---|---|---|---|---|---|---|---|---|---|---|---|---|---|
| 26 | 5.00 | IF | A 0.50 | PPI | 100 | — | 100 | — | | | | | 100 | — |
|  | 5.00 | IF | A 0.50 | PES | 100 | — | 100 | — | | | | | 100 | — |
|  | 5.00 | PPI | A 0.50 | PPI | 100 | — | 100 | — | | | | | 100 | — |
|  | 5.00 | PES | A 0.50 | PES | 90 | 80 | 100 | — | | | | | 100 | — |
|  | 0.5% | ST | A 0.50 | PPI | 90 | — | 100 | — | | | | | 90 | — |
|  | 0.5% | ST | A 0.50 | PES | 90 | 40 | 100 | — | | | | | 100 | — |
| 27 | 5.00 | IF | A 0.50 | PPI | 100 | — | 100 | — | | | | | 100 | — |
|  | 5.00 | IF | A 0.50 | PES | 100 | — | 100 | — | | | | | 100 | — |
|  | 5.00 | PPI | A 0.50 | PPI | 100 | — | 100 | — | | | | | 100 | — |
|  | 5.00 | PES | A 0.50 | PES | 90 | — | 100 | — | | | | | 100 | — |
|  | 0.5% | ST | A 0.50 | PPI | 90 | 80 | 100 | — | | | | | 90 | — |
|  | 0.5% | ST | A 0.50 | PES | 90 | 65 | 100 | — | | | | | 100 | — |
| 28 | 5.00 | IF | A 0.50 | PPI | 100 | — | 100 | — | | | | | 100 | — |
|  | 5.00 | IF | A 0.50 | PES | 100 | — | 100 | — | | | | | 100 | — |
|  | 5.00 | PPI | A 0.50 | PPI | 100 | — | 100 | — | | | | | 100 | — |
|  | 5.00 | PES | A 0.50 | PES | 90 | — | 100 | — | | | | | 100 | — |
|  | 0.5% | ST | A 0.50 | PPI | 90 | — | 100 | — | | | | | 90 | — |
|  | 0.5% | ST | A 0.50 | PES | 90 | 40 | 100 | — | | | | | 100 | — |
| 29 | 5.00 | IF | A 0.50 | PPI | 100 | — | 100 | — | | | | | 100 | — |
|  | 5.00 | IF | A 0.50 | PES | 100 | — | 100 | — | | | | | 100 | — |
|  | 5.00 | PPI | A 0.50 | PPI | 100 | — | 100 | — | | | | | 100 | — |
|  | 5.00 | PES | A 0.50 | PES | 90 | 75 | 100 | — | | | | | 100 | — |
|  | 0.5% | ST | A 0.50 | PPI | 90 | — | 100 | — | | | | | 90 | — |
|  | 0.5% | ST | A 0.50 | PES | 90 | 75 | 100 | — | | | | | 100 | — |
| 30 | 5.00 | IF | A 0.50 | PPI | 100 | — | 100 | — | | | | | 100 | — |
|  | 5.00 | IF | A 0.50 | PES | 100 | — | 100 | — | | | | | 100 | — |
|  | 5.00 | PPI | A 0.50 | PPI | 100 | — | 100 | — | | | | | 100 | — |
|  | 5.00 | PES | A 0.50 | PES | 90 | — | 100 | — | | | | | 100 | — |
|  | 0.5% | ST | A 0.50 | PPI | 90 | — | 100 | — | | | | | 90 | — |
|  | 0.5% | ST | A 0.50 | PES | 90 | 65 | 100 | — | | | | | 100 | — |
| 31 | 5.00 | IF | A 0.50 | PPI | 100 | — | 100 | — | | | | | 100 | — |
|  | 5.00 | IF | A 0.50 | PES | 100 | — | 100 | — | | | | | 100 | — |
|  | 5.00 | PPI | A 0.50 | PPI | 100 | — | 100 | — | | | | | 100 | — |
|  | 5.00 | PES | A 0.50 | PES | 90 | — | 100 | — | | | | | 100 | — |
|  | 0.5% | ST | A 0.50 | PPI | 90 | 75 | 100 | — | | | | | 90 | — |
|  | 0.5% | ST | A 0.50 | PES | 90 | 60 | 100 | — | | | | | 100 | — |
| 32 | 5.00 | IF | A 0.50 | PPI | 100 | — | 100 | — | | | | | 100 | — |
|  | 5.00 | IF | A 0.50 | PES | 100 | — | 100 | — | | | | | 100 | — |
|  | 5.00 | PPI | A 0.50 | PPI | 100 | — | 100 | — | | | | | 100 | — |
|  | 5.00 | PES | A 0.50 | PES | 90 | — | 100 | — | | | | | 100 | — |
|  | 0.5% | ST | A 0.50 | PPI | 90 | — | 100 | — | | | | | 90 | — |
|  | 0.5% | ST | A 0.50 | PES | 90 | 80 | 100 | — | | | | | 100 | — |
| 33 | 5.00 | IF | A 0.50 | PPI | 100 | — | 100 | — | | | | | 100 | — |
|  | 5.00 | IF | A 0.50 | PES | 100 | — | 100 | — | | | | | 100 | — |
|  | 5.00 | PPI | A 0.50 | PPI | 100 | — | 100 | — | | | | | 100 | — |
|  | 5.00 | PES | A 0.50 | PES | 90 | — | 100 | — | | | | | 100 | — |
|  | 0.5% | ST | A 0.50 | PPI | 90 | — | 100 | — | | | | | 90 | — |
|  | 0.5% | ST | A 0.50 | PES | 90 | 70 | 100 | — | | | | | 100 | — |
| 34 | 5.00 | IF | A 0.50 | PPI | 100 | — | 100 | — | | | | | 100 | — |
|  | 5.00 | IF | A 0.50 | PES | 100 | — | 100 | — | | | | | 100 | — |
|  | 5.00 | PPI | A 0.50 | PPI | 100 | — | 100 | — | | | | | 100 | — |
|  | 5.00 | PES | A 0.50 | PES | 90 | 65 | 100 | — | | | | | 100 | — |
|  | 0.5% | ST | A 0.50 | PPI | 90 | — | 100 | — | | | | | 90 | — |
|  | 0.5% | ST | A 0.50 | PES | 90 | 45 | 100 | — | | | | | 100 | — |
| 35 | 5.00 | IF | A 0.50 | PPI | 100 | — | 100 | — | | | | | 100 | — |
|  | 5.00 | IF | A 0.50 | PES | 100 | — | 100 | — | | | | | 100 | — |
|  | 5.00 | PPI | A 0.50 | PPI | 100 | — | 100 | — | | | | | 100 | — |
|  | 5.00 | PES | A 0.50 | PES | 90 | — | 100 | — | | | | | 100 | — |
|  | 0.5% | ST | A 0.50 | PPI | 90 | — | 100 | — | | | | | 90 | — |
|  | 0.5% | ST | A 0.50 | PES | 90 | 60 | 100 | — | | | | | 100 | — |
| 36 | 5.00 | IF | A 0.50 | PPI | 100 | — | 100 | — | | | | | 100 | — |
|  | 5.00 | IF | A 0.50 | PES | 100 | 60 | 100 | — | | | | | 100 | — |
|  | 5.00 | PPI | A 0.50 | PPI | 100 | — | 100 | — | | | | | 100 | — |
|  | 5.00 | PES | A 0.50 | PES | 90 | 80 | 100 | — | | | | | 100 | — |
|  | 0.5% | ST | A 0.50 | PPI | 90 | — | 100 | — | | | | | 90 | — |

TABLE IV-continued
N—(BENZENESULFONYL) CARBAMATES
ANTIDOTAL AND HERBICIDAL EFFECTIVENESS

| Cmpd. No. | Antidote Application Rate | Antidote Application Method | Herbicide Application Rate | Herbicide Application Method | % Injury Soybeans U | % Injury Soybeans T | % Injury Watergrass U | % Injury Watergrass T | % Injury Mustard U | % Injury Mustard T | % Injury Curly Dock U | % Injury Curly Dock T | % Injury Johnsongrass U | % Injury Johnsongrass T |
|---|---|---|---|---|---|---|---|---|---|---|---|---|---|---|
| | 0.5% | ST | A 0.50 | PES | 90 | 60 | 100 | — | | | | | 100 | — |

KEY TO TABLE IV
Methods of Application:
PPI = preplant incorporation
IF = infurrow surface spray
PES = pre-emergence surface spray
ST = seed treatment
Herbicides:
A = 3-(3',4'-dichlorophenyl)-1,1-dimethylurea
B = 1-(m-t-butylacetamidophenyl)-3-methyl-3-methoxyurea
U = antidotally untreated
T = antidotally treated
— = no change
Omitted compound numbers are those compounds of Table I which showed no antidote activity at any of the levels tested.

FORMULATIONS

The object of the formulation is to apply the compositions to the locus where control is desired by a convenient method. The "locus" may include soil, seeds, seedlings, and vegetation.

The amount of antidote compound which comprises part of a herbicidal composition will generally range from approximately 0.001 to 30 parts by weight per weight of the herbicidal compound.

Formulations will generally contain several additives. Among these are some inert ingredients and diluent carriers such as organic solvents, water, oil and water, water in oil emulsions, carriers of dusts and granules, and surface active wetting, dispersing, and emulsifying agents.

Fertilizers, e.g., ammonium nitrate, urea and superphosphate, may also be included.

Aids to rooting and growth, e.g., compost, manure, humus, sand, etc., may likewise be included.

The formulations are commonly dusts, wettable powders, granules, solutions or emulsifiable concentrates.

Dusts are free-flowing powder compositions containing the herbicidal compound impregnated on a particulate carrier. The particle size of the carriers is usually in the approximate range of 30 to 50 microns. Examples of suitable carriers are talc, bentonite, diatomaceous earth, and pyrophyllite. Anti-caking and anti-static agents can be added, if desired. The composition generally contains up to 50% of active ingredient. Dusts, like liquid compositions, can be applied by spraying from boom and hand sprayers or airplanes.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols; in which the alcohol groups are free, omega-substituted polyethylene glycols of relatively long chain length. A list of surface active agents suitable for use in agriculture formulations can be found in Wade Van Valkenburg, Pesticide Formulations (Marcel Dekker, Inc., N.Y., 1973) at pages 79-84.

Granules comprise the herbicidal composition impregnated on a particulate inert carrier having a particle size of about 1 to 2 millimeter (mm) in diameter. The granules can be made by spraying a solution of the active ingredient in a volatile solvent onto the granular carrier. Suitable carriers in preparation of granules include clay, vermiculite, sawdust, granular carbon, etc.

The herbicidal compositions can also be applied to the soil in the form of a soolution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compounds and compositions of this invention can also be applied by addition to irrigation water supplied to the field to be treated. This method of application permits the penetration of the compositions into the soil as the water is absorbed therein.

It is not necessary that the compounds and compositions be admixed with the soil particles. After application by the above discussed methods, they may be distributed below the surface to a depth of at least one-half inch by conventional means such as discing, dragging, or mixing.

We claim:
1. A composition comprising
   (a) an herbicidally effective amount of an urea of the formula

$$R-NH-\overset{\overset{O}{\|}}{C}-N\diagup^{R_1}_{\diagdown R_2}$$

in which
   R is selected from the group consisting of phenyl and substituted phenyl, wherein the substitutents are acylamido having from 2 to 10 carbon atoms, inclusive;
   $R_1$ is selected from the group consisting of hydrogen and 1-4 carbon alkyl; and
   $R_2$ is selected from the group consisting of 1-4 carbon alkyl and 1-4 carbon alkoxy; and (b) a non-phytotoxic but antidotally effective amount of N-(benzenesulfonyl) carbamate of the formula

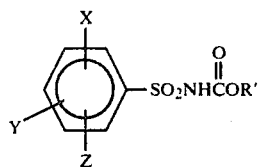

in which
X and Y are independently selected from the group consisting of hydrogen and methyl;
Z is selected from the group consisting of hydrogen, methyl, chloro, and trifluoromethyl; and
R' is selected from the group consisting of 1-4 carbon alkyl, 1-4 carbon haloalkyl, 3-6 carbon alkenyl, 3-6 carbon haloalkenyl and 3-6 carbon alkynyl.

2. A composition according to claim 1 in which R is m-t-butylacetamido phenyl, $R_1$ is methyl, and $R_2$ is methoxy.

3. A composition according to claim 2 in which X and Y are each hydrogen, Z is chloro, and R' is methyl.

4. A composition according to claim 2 in which X and Y are each hydrogen, Z is chloro, and R' is 2,2,2-trifluoroethyl.

5. A method of controlling undesirable vegetation and protecting soybeans from urea-type herbicidal injury which comprises applying to a locus where control is desired.
(a) an herbicidally effective amount of an urea of the formula

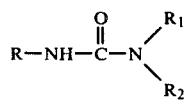

in which
R is selected from the group consisting of phenyl and substituted phenyl, wherein the substituents are acylamido having from 2 to 10 carbon atoms, inclusive;
$R_1$ is selected from the group consisting of hydrogen and 1-4 carbon alkyl; and
$R_2$ is selected from the group consisting of 1-4 carbon alkyl and 1-4 carbon alkoxy; and
(b) a non-phytotoxic but antidotally effective amount of N-(benzenesulfonyl) carbamate of the formula

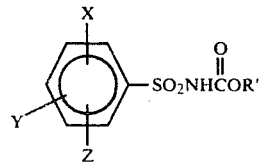

in which
X and Y are independently selected from the group consisting of hydrogen and methyl;
Z is selected from the group consisting of hydrogen, methyl, chloro, and trifluoromethyl; and
R' is selected from the group consisting of 1-4 carbon alkyl, 1-4 carbon haloalkyl, 3-6 carbon alkenyl, 3-6 carbon haloalkenyl and 3-6 carbon alkynyl.

6. A method according to claim 5 in which R is m-t-butylacetamido phenyl, $R_1$ is methyl and $R_2$ is methoxy.

7. A method according to claim 6 in which X and Y are each hydrogen, Z is p-chloro, and R' is methyl.

8. A method according to claim 6 in which X and Y are each hydrogen, Z is m-chloro, and R' is 2,2,2-trifluoroethyl.

9. Soil treated with a composition comprising
(a) an herbicidally effective amount of a urea-type herbicide of the formula

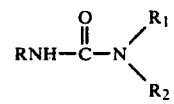

in which
R is selected from the group consisting of phenyl and substituted phenyl, wherein the substituents are acylamido having from 2 to 10 carbon atoms, inclusive;
$R_1$ is selected from the group consisting of hydrogen 1-4 carbon alkyl; and
$R_2$ is selected from the group consisting of 1-4 carbon alkyl and 1-4 carbon alkoxy; and
(b) a non-phytotoxic antidotally effective amount of a compound of the formula

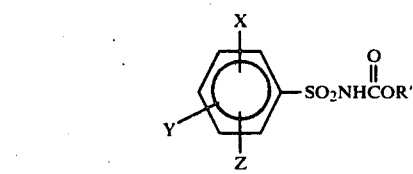

in which
X and Y are independently selected from the group consisting of hydrogen and methyl;
Z is selected from the group consisting of hydrogen, methyl, chloro, and trifluoromethyl; and
R' is selected from the group consisting of 1-4 carbon alkyl, 1-4 carbon haloalkyl, 3-6 carbon alkenyl, 3-6 carbon haloalkenyl, and 3-6 carbon alkynyl.

10. A herbicidal composition comprising
(a) a herbicidally effective amount of an urea herbicide of the formula

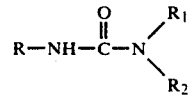

in which
R is selected from the group consisting of phenyl and substituted phenyl, wherein the substituents are acylamido having from 2 to 10 carbon atoms, inclusive;
$R_1$ is selected from the group consisting of hydrogen and 1-4 carbon alkyl; and
$R_2$ is selected from the group consisting of 1-4 carbon alkyl and 1-4 carbon alkoxy; and
(b) a non-phytotoxic but antidotally effective amount of a N-(benzenesulfonyl) carbamate of the formula

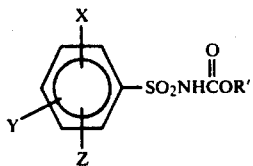

in which X and Y are independently selected from the group consisting of hydrogen and methyl;
Z is selected from the group consisting of hydrogen, methyl, chloro, and trifluoromethyl; and
R' is selected from the group consisting of 1-4 carbon alkyl, 1-4 carbon haloalkyl, 3-6 carbon alkenyl, 3-6 carbon haloalkenyl and 3-6 carbon alkynyl.

* * * * *

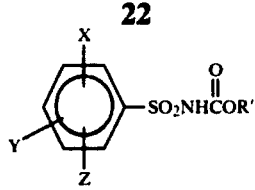

in which X and Y are independently selected from the group consisting of hydrogen and methyl;
Z is selected from the group consisting of hydrogen, methyl, chloro, and trifluoromethyl; and
R' is selected from the group consisting of 1-4 carbon alkyl, 1-4 carbon haloalkyl, 3-6 carbon alkenyl, 3-6 carbon haloalkenyl and 3-6 carbon alkynyl.

* * * * *